April 2, 1946. E. S. BOERNER Plant Pat. 673
ROSE PLANT
Filed June 1, 1945
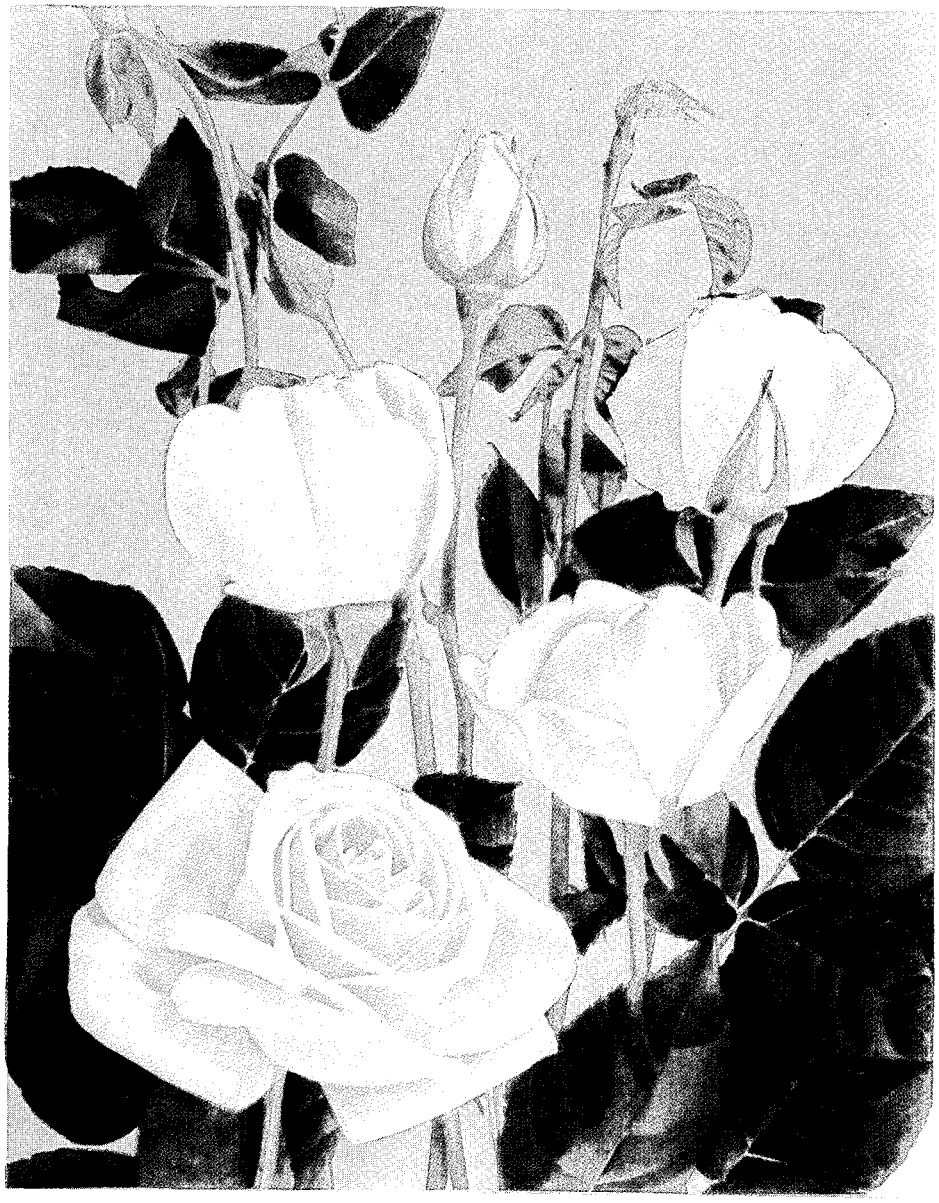
Inventor
E. S. Boerner
By Robbins Robb
His attorneys Patented Apr. 2, 1946

UNITED STATES PATENT OFFICE

673

ROSE PLANT

Eugene S. Boerner, Newark, N. Y., assignor to Jackson & Perkins Company, Newark, N. Y., a corporation of New York Application June 1, 1945, Serial No. 597,001

1 Claim. (Cl. 47—61)

The present invention relates to a new and distinct variety of rose plant of the Hybrid Tea class and is predominantly characterized as to novelty by the shape and color features of its blossoms and other distinctions of the plant hereinafter set forth.

More specifically, the flowers of this new rose are large and cup-shaped and of a Deep Rose Pink overcast by Primrose Yellow extending up from the base of the petal. Its identity is more particularly evidenced by the white striping on the mid-rib of the petaloids and the last row of petals before the petaloids.

A further important characteristic of the flowers is observed in the heavy veining on the outside of the outer petals.

This new variety is further notable for its vigorous greenhouse growth and the characteristic of slight burning of the ends of its foliage at certain times.

These features of novelty combined with the distinctive penetrating fragrance of the flowers make this new rose an outstanding and attractive variety among today's roses.

Asexual reproduction of this new variety shows the foregoing characteristics come true to form and are established.

The drawing shows specimens of this variety in various stages of development.

The following is a detailed description of the new variety, the color terminology being in accordance with Ridgway's Color Standard.

Parentage: Seedling.

*Seed parent.*—(Royal Red x Talisman) x unnamed red seedling.

*Pollen parent.*—Very vigorous hardy Pink seedling (Talisman x Nutneyron).

Classification: Botanic and commercial—Hybrid Tea.

*Flower*

(Observations made in the fields of Jackson & Perkins Company, Newark, New York, in the morning in the month of September, 1944.)

Blooming habit: Recurrent—continuous.

Bud:

*Size.*—Large.

*Form.*—Long; pointed. Is not affected by wet or hot weather.

*Color.*—When sepals first divide—Pomegranate Purple, Plate XII; when petals begin to unfurl—Spinel Red, Plate XXVI; when half blown—inside of petals, Rose Color, Plate XII, overcast with Tyrian Rose, Plate XII. The pencilled veins on the inside of the petal are Tyrian Rose, Plate XII. The Pale Lemon Yellow, the color of the aiglet and base of the petal, diffuses up into the petal, Plate IV. Reverse of petals, Spinel Pink, Plate XXVI—the more prominent veins and mid-rib on the outside Tyrian Rose, Plate XII.

*Sepals.*—Slightly branched. Curl back when petals begin to unfurl. *Color*—inside—Kildare Green, Plate XXXI; outside—Biscay Green, Plate XVII.

*Calyx.*—Shape—funnel. Size—long. Aspect—smooth. Color—Lettuce Green, Plate V.

*Peduncle.*—Length—medium. Aspect—prickly. Color—Lettuce Green, Plate V. Strength—stiff; heavy.

*Opening.*—Opens up well. Is not affected by adverse conditions.

Bloom:

*Size.*—Large. Average size when fully expanded, 4½ to 5 inches.

*Borne.*—Singly and several together.

*Stems.*—Long; strong.

*Form.*—When first open—cupped. Permanence—retains its form to the end.

*Petalage.*—Double (full but open center). Number of petals under normal conditions, 35 to 40.

*Color.*—Center of flower—Deep Rose Pink, Plate 12. Outer petals—Deep Rose Pink, Plate 12. Base of petals (aiglet)—Picric Yellow, Plate IV. Inside of petals—Deep Rose Pink, Plate XII, with an overcast of Primrose Yellow, Plate XXX, from the base. Reverse of petals—Thulite Pink, Plate XXVI. General tonality from a distance—Deep Rose Pink, Plate XII.

*Variegations.*—Outside of petals distinctly veined with Tyrian Pink, Plate XII. The last row of petals before petaloids show distinct striping.

*Discoloration.*—General tonality at end of first day—Deep Rose Pink, Plate XII. Second day—Thulite Pink, Plate XXVI. Third day—Rose Pink, Plate XII.

Petals:

*Texture.*—Leathery. Is not affected by wet or hot weather.

*Appearance.*—Inside—velvety. Outside—satiny.

*Form.*—Oval.

*Arrangement.*—Imbricated (regularly arranged shinglelike). Petaloids in center—few; small.

*Persistence.*—Drop off cleanly.

*Fragrance.*—Strong. Nature—Strong Tea (average Hybrid Tea scent).

*Lasting quality.*—On the plant and as cut flower, long.

Genital organs:

*Stamens, anthers.*—Size—large; many. Color—Mustard Yellow, Plate XVI. Arrangement—regular around styles.

*Stamens, filaments (threads).*—Length—long. Color—Spinel Red, Plate XVI.

*Pollen.*—Straw Yellow, Plate XVI.

*Styles.*—Bunched, uneven length; medium length; thin.

*Stigmas.*—Cream color, plate XVI.

*Ovaries.*—All enclosed in calyx.

*Plant*

Form: Bush.

Growth: Vigorous; upright.

Foliage: 5 leaflets.

*Size.*—Large.

*Quantity.*—Abundant.

*Color.*—New foliage: upper side—Oil Yellow, Plate V, overcast with Hay's Russet, Plate XIV; under side—Hay's Russet, Plate XIV. Old foliage: upper side—Cress Green, Plate XXXI; under side in Light Cress Green, Plate XXXI.

*Shape.*—Oval pointed.

*Texture.*—Upper side—leathery. Under side—rough. Ribs and veins—ordinary.

*Edge.*—Serrated (saw toothed).

*Serration.*—Single; small.

*Rachis.*—Cress Green, Plate XXXI. Under side—smooth.

*Stipules.*—Long; bearded.

*Disease resistance.*—Resistant; when used in greenhouse, edge of foliage is susceptible to burning.

Wood:

*New wood.*—Color—Yellowish Citrine, Plate XVI. Bark—smooth.

*Old wood.*—Color—Jade Green, Plate XXXI. Bark—smooth.

Thorns (thorns are divided into thorns, prickles and short needles):

*Thorns.*—Quantity—on main stalks from base—few; on laterals from stalk—none. Form—narrow base; medium length; hooked downward. Color when young—Corinthian Red, Plate XXVII. Position—irregular.

*Prickles.*—On main stalks and on laterals—none.

*Short needles.*—On main stalks and on laterals—none.

I claim:

A new and distinct variety of Rose plant characterized as to novelty by its large cup-shaped Pink flowers having white stripes on the midribs of certain of its petals and heavy veins on the outside of its outer petals; by the vigorous greenhouse growth of the plant and tendency to show slight burning of the ends of its foliage; and by the penetrating fragrance of its flowers, substantially as shown and described.

EUGENE S. BOERNER.